(12) United States Patent
Kinmon et al.

(10) Patent No.: US 8,679,123 B2
(45) Date of Patent: Mar. 25, 2014

(54) SURGICAL DEVICE, SYSTEM AND METHOD OF USE THEREOF

(75) Inventors: Kyle Kinmon, Boca Raton, FL (US); Daniel Halme, Warren, NJ (US)

(73) Assignee: Mbrace, LLC, Boca Raton, FL (US)

( * ) Notice: Subject to any disclaimer, the term of this patent is extended or adjusted under 35 U.S.C. 154(b) by 863 days.

(21) Appl. No.: 12/275,133

(22) Filed: Nov. 20, 2008

(65) Prior Publication Data

US 2010/0125275 A1    May 20, 2010

(51) Int. Cl.
  *A61B 17/56*  (2006.01)
  *A61B 17/58*  (2006.01)
  *A61B 17/064* (2006.01)
  *A61B 17/84*  (2006.01)
  *A61F 2/30*   (2006.01)

(52) U.S. Cl.
  USPC .............................................. 606/75; 606/219

(58) Field of Classification Search
  USPC ............................................ 606/75, 219, 220
  See application file for complete search history.

(56) References Cited

U.S. PATENT DOCUMENTS

| | | | |
|---|---|---|---|
| 2,222,517 A * | 11/1940 | Price | 606/99 |
| 3,960,147 A | 6/1976 | Murray | |
| 4,414,967 A | 11/1983 | Shapiro | |
| 5,053,038 A | 10/1991 | Sheehan | |
| 5,662,655 A | 9/1997 | Laboureau | |
| 5,779,707 A | 7/1998 | Bertholet | |
| 5,785,713 A | 7/1998 | Jobe | |
| 6,059,787 A | 5/2000 | Allen | |
| 6,179,840 B1 | 1/2001 | Bowman | |
| 6,348,054 B1 | 2/2002 | Allen | |
| 6,402,757 B1 | 6/2002 | Moore | |
| 6,592,587 B1 | 7/2003 | Roger | |
| 6,783,531 B2 | 8/2004 | Allen | |
| 7,214,232 B2 | 5/2007 | Bowman | |
| 2002/0019636 A1 * | 2/2002 | Ogilvie et al. | 606/75 |
| 2003/0167072 A1 | 9/2003 | Oberlander | |
| 2007/0093839 A1 | 4/2007 | Beckendorf | |
| 2007/0276388 A1 | 11/2007 | Robertson | |

* cited by examiner

*Primary Examiner* — Nicholas Woodall
*Assistant Examiner* — Christine Nelson
(74) *Attorney, Agent, or Firm* — Trojan Law Offices

(57) ABSTRACT

The present invention includes a surgically implantable compression staple, system, and method of use thereof for the internal fixation of bone fractures, fusions, and osteotomies. The staple has a grooved construction along the outside edge of each of its legs and cannulated tabs are aligned above the grooves. The grooves and cannulated tabs of the staple are sized to fit and align with guide wires. Once holes are drilled over the guide wires with a specialized cannulated drill, the appropriately sized staple can be inserted over the guide wires and the guide wires are subsequently removed. The compression feature of the staple is activated and the staple provides stability across the desired fractured site. The system and method allows for easy alignment and precise placement of surgically implantable staples.

11 Claims, 5 Drawing Sheets

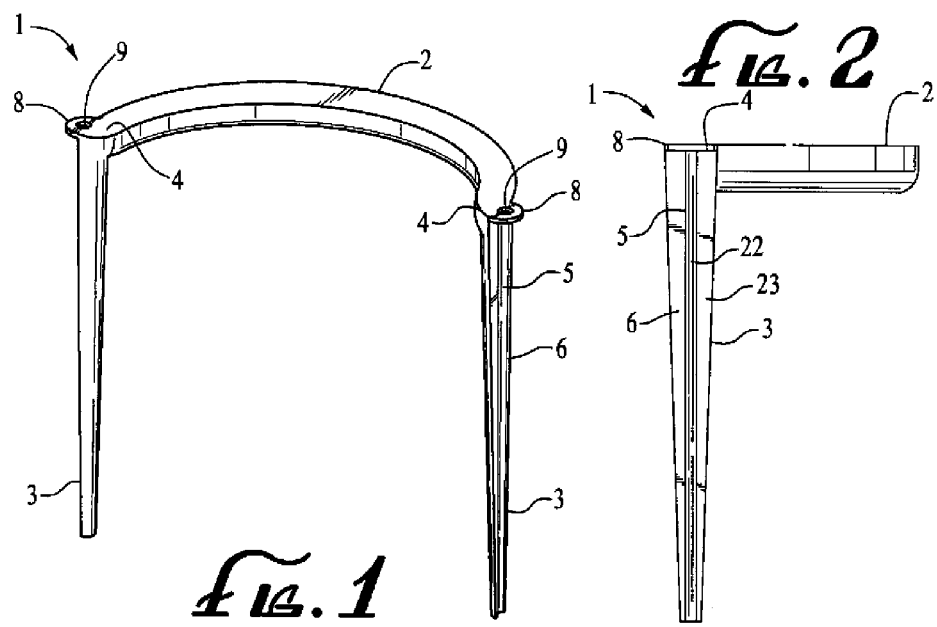
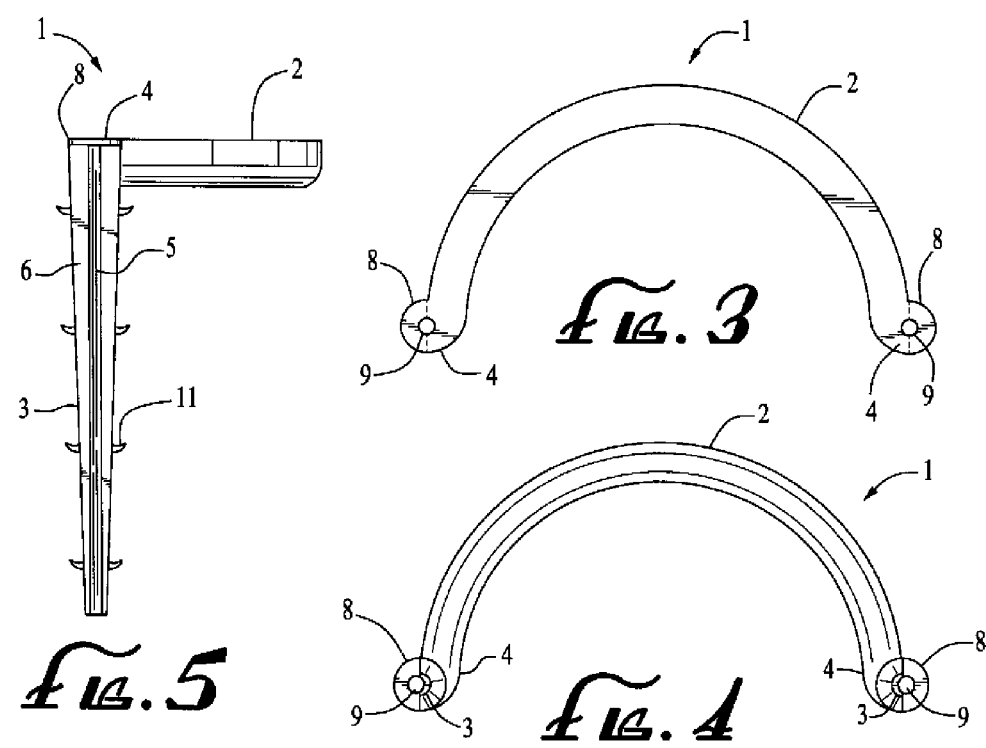

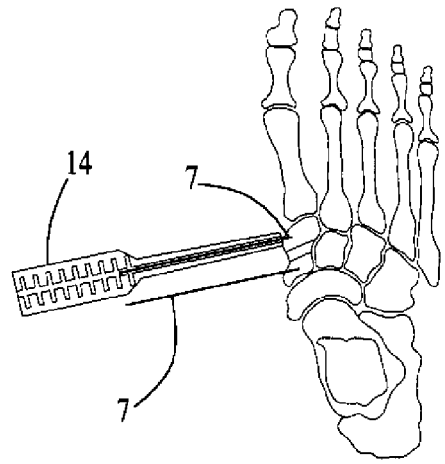
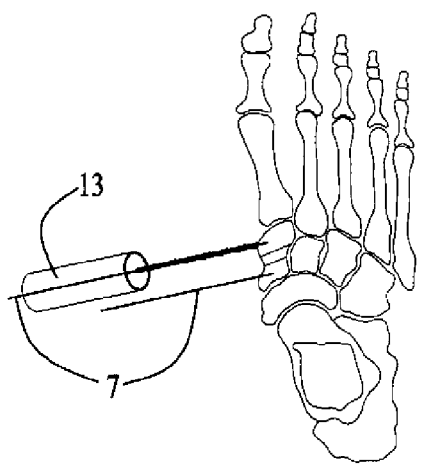
FIG. 6F  FIG. 6G
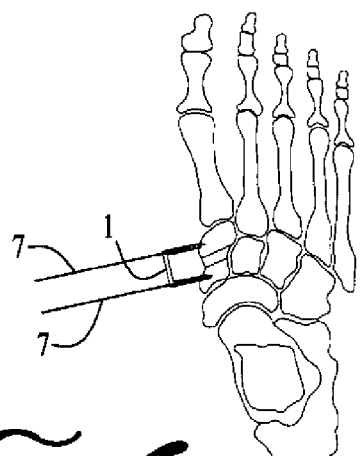
FIG. 6H
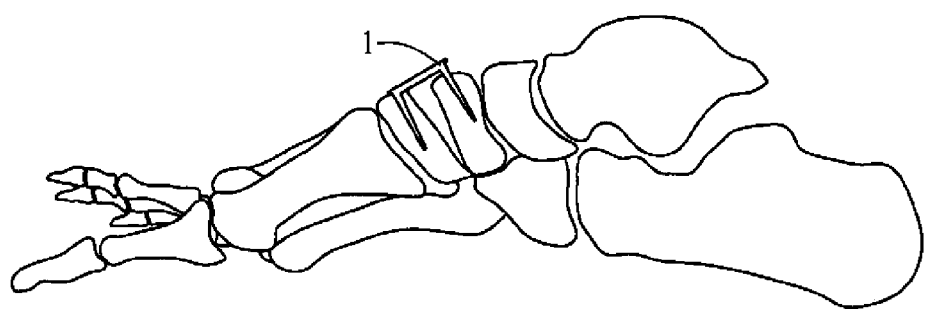
FIG. 6I

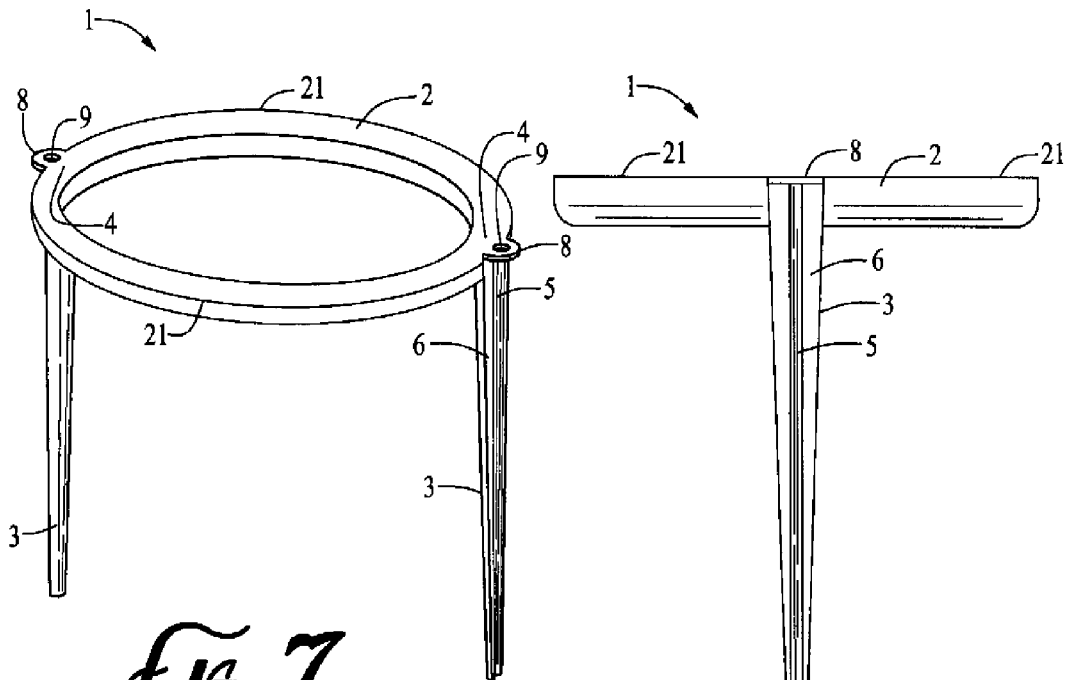
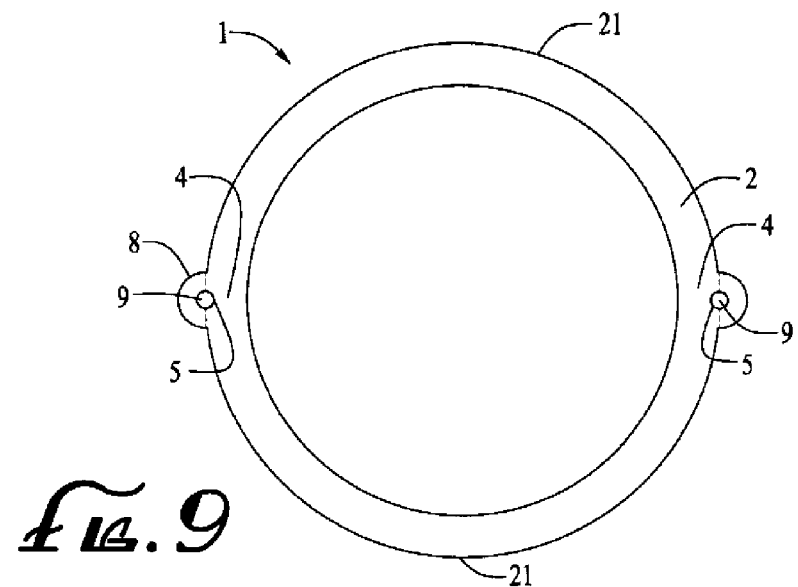

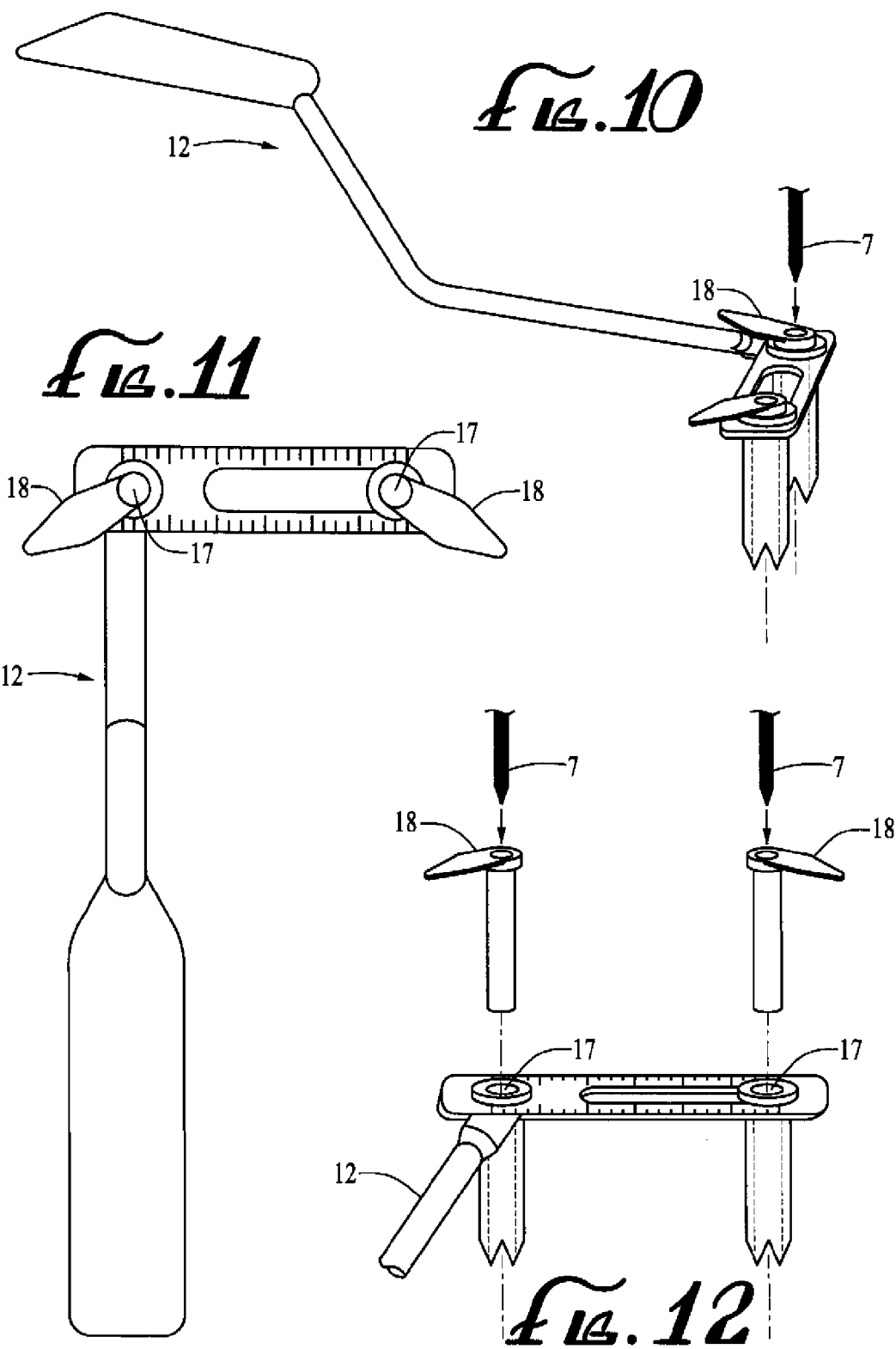

SURGICAL DEVICE, SYSTEM AND METHOD OF USE THEREOF

FIELD OF THE INVENTION

The present invention relates to a surgical device, system, and method of use thereof. More specifically, the invention relates to a grooved and tabbed surgical staple, related tools, and a method for its easy insertion into bone or tissue during orthopedic surgical procedures.

BACKGROUND OF THE INVENTION

Surgical staples, such as compression staples used to stabilize bones during orthopedic surgical procedures, are well known in the art. To correct and heal bone fractures properly, staples are often used to keep bone fragments in position by compressing and holding the bone fragments together without motion. Various staples have been produced to provide compression in various manners.

For example, U.S. Pat. Nos. 6,059,787, 6,348,054, 6,783,531 describe surgical staples and methods that use a spring-type force to create a compression effect. The staples disclosed in these patents require the spreading apart of the staples' legs to create a spring-type force before applying a percussive force to drive the staples into the bone with a resultant compressive effect. Similarly, U.S. Pat. No. 5,785,713 discloses a staple, which has the staple's legs in an initial angled orientation, and the legs must be spread apart to a parallel configuration before inserting the staple into bone. However, fractures may arise from driving the compound-shaped legs into the bone. Also, the mechanism employed for such staples is less than optimal in that the staple's legs converge at their ends to create compression, which provides little to no compression at the bridge end of the staple.

U.S. Patent Application Publication No. 2007/0276388 discloses surgical staples and annulus closure tools, having two to four legs, for sealing inter-vertebral disk incisions or herniations. A disadvantage of all of the aforementioned staples is that the percussive force applied to drive the staples is quite abrasive and a more controllable method of insertion would be a more advantageous surgical technique. Also, there is no guidance prior to insertion for the precise placement of the staples.

U.S. Pat. No. 4,994,063 describes a method and bone staple for interosseous bone fixation. Such staples and methods, however, have common insertion techniques that are extremely difficult to complete. A typical technique initially requires drilling holes for a staple using a drill guide. The drill guide is removed before inserting the staple. In many cases the holes are lost due to blood, debris, and soft issue in the surrounding area that fill into the holes. Thus, it is difficult to accurately assess the location of the holes under fluoroscopy using this technique. For these reasons, staples are placed inaccurately and the holes must be re-drilled to properly insert the staple and repair the bone.

As an attempt to overcome this problematic insertion technique in the field, surgical devices that may be cannulated and used with guides have been introduced. However, such attempts are problematic for other reasons. For example, U.S. Patent Application Publication No. 2007/0093839 describes a compression staple for securing tissue. The two legs of the staple may be cannulated and the reference teaches the following method of insertion: a first guide pin is driven into the first tissue; one of the legs of the staple is inserted over the first guide pin; the staple is aligned in the desired position; a second guide pin is driven into the second tissue; the second staple leg is inserted over the second guide pin, and finally; the staple is driven into the tissue. The prior art fails to teach an easy method of insertion that provides for precise placement of both legs of the staple at the same time. Further, predrilled holes are not used for placement of the staple and the staple must be driven into the bone with percussive force. Another disadvantage of cannulated staples is that they have hollow anchoring members and thus provide a weak structure for purposes of holding bone fragments together. The current devices do not disclose a robust staple or an insertion technique that is precise, quick, not destructive to the bone, and easy.

Therefore, what is needed in the art is an improved surgical staple with increased strength and an improved method that allows for easy and precise insertion into bones or tissues compared with the current methodologies known in the art. With these goals in mind, the inventor has created a robust staple with improved structural properties and fixation capabilities, as well as an easy and effective insertion technique and system thereof for stabilizing bones with compression staples during orthopedic and podiatric type surgical procedures.

SUMMARY OF THE INVENTION

The present invention describes a grooved and tabbed compression staple. The invention also describes a system of tools for its insertion into bone as well as a method for its insertion. In one embodiment, the surgical staple for fastening bones, tissues, or fragments thereof, comprises a bridge having a first leg and a second leg extending from a same side of the bridge. Each leg has at least an inner elevation and an outer elevation along its length. The legs are capable of receiving a guide wire between the inner and said outer elevations such that said staple is guided by said guide wires when a user inserts said staple over said guide wires and into bone or tissue during a surgical procedure. The bridge can further comprise a first and second tab extending therefrom, wherein each tab has an aperture therethrough so that the legs and tabs of the staple are capable of receiving a guide wire such that said staple is guided by said guide wires when a user inserts said staple over said guide wires and into bone or tissue during a surgical procedure.

The surgical staple can also be described as comprising a middle bridge portion, having a first end and a second end, a first leg extending from said first end of the bridge, and a second leg extending from said second end of the bridge. The first and second legs each have at least two elevations along the length of each leg. Optionally, tabs extend from each of the middle bridge portion, wherein each tab includes a hole therethrough. The optional tabs can also extend down the length of staple, thereby forming a hole through the length of each staple leg. These tabs that extend down the length of the staple need not extend down the length of each leg in its entirety. The first and second legs and the optional tabs of the staple are capable of aligning with and receiving a guide wires such that the staple is guided by the guide wires when a user inserts the staple over the guide wires and into bone or tissue during a surgical procedure.

In another embodiment, the staple's legs are oriented in a substantially parallel position. In yet another embodiment, the staple's legs are oriented in a converging position. The at least two elevations of each staple leg can be formed along the outer or inner edge of each leg. The staple can be made of a material selected from a group consisting of memory metal, memory alloy, metal material, alloy, and a material capable of being manually compressed by the user.

The bridge of the staple can be curved in an upwards or sideways direction so that the bridge is either parallel or perpendicular to the staple's legs, respectively. In an alternative embodiment, the bridge forms a substantially circular shape and is perpendicular to the staple's legs. The staple's legs can have a plurality of projections protruding therefrom.

A surgical device system is also disclosed, comprising any embodiments of the surgical staple as described above, a plurality of guide wires, and a drill. The drill has a drill bit with a hole axially running through it. A user can insert the guide wires into bone fragments, place the drill bit over the guide wires and thereby receive the wire through the hole in the drill bit to bore holes around the guide wires and into the bone fragments, remove the drill, insert the surgical staple over said guide wires and into said holes in the bone, and remove the guide wires, so as to insert the surgical staple into the bone fragments to repair a bone fracture.

In another embodiment, the surgical device system can include a guide device, whereby a user can place the guide device in a desired position over a bone fracture, insert at least one guide wire through the guide device and into bone fragments, remove the guide device, place the drill bit over the guide wires and thereby receive the wire through the hole in the drill bit to bore holes around the guide wires and into the bone fragments, remove the drill, insert the surgical staple over the guides wires and into said holes in said bone, and remove the guide wires, thereby inserting the surgical staple into the bone fragments to repair the bone fracture. The guide device can include an assembly that is capable of inserting two guide wires at a predetermined width, wherein the width of the assembly is adjustable, and a user can select a desired width to guide insertion of the guide wires into bone.

The guide device can include an adjustable assembly, wherein said adjustable assembly further comprises at least one aperture capable of accepting a drill, and wherein said apertures further comprise detachably attachable inserts capable of accepting at least one guide wire. The user can place the guide device in a desired position over a bone fracture, adjust the positions of the apertures having inserts attached to guide insertion of said guide wires into bone. The user can then insert guide wires through these inserts of the apertures and into bone fragments and remove the inserts while leaving the guide device in place. The user can then use the guide device to accept a drill therethrough, wherein the drill has a drill bit with a hole running axially through it, and can thus place the drill bit over the guide wires to bore holes around the guide wires and into the bone fragments. After the holes are drilled, the drill and guide device can be removed so that the staple can be inserted over the guide wires and into the bone. Afterwards, the user can remove the guide wires, thereby inserting the staple into the bone fragments and repairing a bone fracture.

In yet another embodiment, the system can include a depth gauge, whereby a user can measure the length of the guide wire's insertion and thereby select a desired length of the staple's legs for insertion into bone. The system can also include a staple compression device, whereby a user can insert the staple compression device into the holes of the tabs of the staple and thereby compress the staple's legs towards one another to further aid compression of the surgical staple. A device, such as a tamp or mallet can be used to seat the staple into bone.

A method for using a surgical staple is also disclosed. According to the method, the practitioner places two guide wires in bone, in a desired position on each side of a bone fracture. Holes are bored into the bone fragments over the two guide wires, a grooved and tabbed surgical staple is aligned with the guide wires and inserted into the holes in the bone. The guide wires are removed and the staple is compressed so that the staple stabilizes the bone fragments to repair a bone fracture. The insertion of the guide wires can be aided by placing a guide device over the bone fracture. The holes in the bone can be bored with a cannulated drill placed over the guide wires and the guide wires' positions can be confirmed fluoroscopically. Further, a depth gauge can be used to measure the exposed length of the inserted guide wires to determine the length of the staple's legs to be used. A device such as a mallet or tamp can be used to seat the inserted grooved and tabbed surgical staple and the staple's position can be confirmed fluoroscopically.

BRIEF DESCRIPTION OF THE DRAWINGS

FIG. 1 is a side perspective view of a surgical staple according to the present invention;

FIG. 2 is a side orthogonal view of a surgical staple according to the present invention;

FIG. 3 is a top orthogonal view of a surgical staple according to the present invention;

FIG. 4 is a bottom orthogonal view of a surgical staple according to the present invention;

FIG. 5 is a side orthogonal view of one embodiment of a surgical staple according to the present invention;

FIGS. 6A-6I depict a system and steps of a method for inserting a surgical staple for repairing bone fractures in accordance with the present invention;

FIG. 7 is a side perspective view of a surgical staple according to the present invention;

FIG. 8 is a side orthogonal view of a surgical staple according to the present invention;

FIG. 9 is a top orthogonal view of a surgical staple according to the present invention;

FIG. 10 is a side perspective view of a guide device according to the present invention;

FIG. 11 is a top orthogonal view of a guide device according to the present invention; and FIG. 12 is a side perspective view of an adjustable assembly of a guide device according to the present invention.

DETAILED DESCRIPTION OF THE INVENTION

Figure 6A:
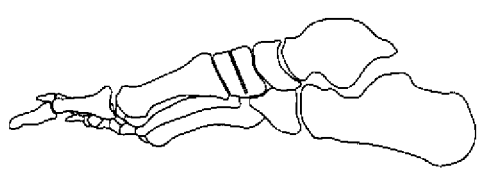

The present invention overcomes disadvantages of the prior art, as identified and disclosed by the inventor, by providing an improved compression staple and an easy-to-use system and method for its insertion for the internal fixation of bone fractures, fusions, and osteotomies. More specifically, the present invention includes a robust grooved and tabbed surgically implantable staple and can be easily inserted over guide wires and across a fractured bone to provide stability and compression across the desired site. The compression staple can be made of a shape memory metal material or alloy, such as nickel titanium, or another metal material or alloy, such as stainless steel or titanium. The staple is preferably made of a non-corrodable metal material compatible with use in the body. The staple may also be made of a bio-absorbable material. Other materials used for bone fixation include vitalium, chrome cobalt, and suitable bio-compatible polymeric materials.

Different embodiments of the staple 1 are illustrated in FIGS. 1-5. As shown in FIG. 1, the staple 1 includes a bridge 2, e.g., a middle bridge portion, and two legs 3 at each end 4 of the bridge portion 2 that extend substantially perpendicular to the middle bridge portion 2. The legs 3 of the staple 1 can be formed in any shape, including, but not limited to, a flat shape or a circular shape. Because the staple's legs 3 can be substantially parallel, the compression is more evenly distributed throughout the staple, whereas staples like those in the prior art that have legs converging towards one another provide little to no compression at the bridge 2 end of the staple 1. The legs 3 of the staple can also be converging towards one another, especially when using a staple 1 made from a shape memory material. The legs 3 of the staple 1 are substantially solid and have at least two elevations, an inner elevation 22 and an outer elevation 23, that run down the length of each staple leg 3. The inner elevation 22 can be defined as the inner most surface of the leg 3. The outer elevation 23 can be defined as the outer most surface of the leg 3.

As shown in FIG. 1, the inner elevation and outer elevation can form U-shaped grooves 5 that run down the entire length of each staple leg 3, however, it is not necessary that a U-shaped groove be formed nor that the grooves 5 be formed along the entire length of each staple leg 3. The inner elevation and outer elevation can also form an L-shaped groove 5 along the length of each staple leg 3 (not shown). The bridge-to-leg interface 4 is solid, therefore the staple 1 avoids any problems of weakness or breakage in the staple's legs 3 or bridge-to-leg interface 4 that hollow or cannulated staple legs can create. The legs 3 of the staple 1 can be tapered or not tapered towards the ends of the legs 3 that are distal from the bridge 2. Also, the distal ends of legs 3 of the staple can be blunt or formed to an acute point.

The grooves 5 that run down the length of each leg 3 of the staple can run down the outer edges 6 of the legs 3. Alternatively, the grooves 5 can run down the inner edges of each of the legs 3 (not shown). The grooves 5 can also be described as a recess. The function of the groove 5 is served so long as the leg 3 has at least two elevations relative to the central axis of the leg.

The efficiency and effectiveness of orthopedic stapling is considerably improved when the staple 1 and associated instruments are used in conjunction with guide wires 7. Accordingly, the shape and diameter of the grooves 5 coincide with the shape and diameter of the guide wires 7 in which the staple 1 is inserted over. For example, as illustrated in FIG. 1, the grooves 5 are in a semi-circular shape. In addition, at each end 4 of the bridge 2 of the staple 1 is a tab 8 with a hole 9 in each tab 8 equal to or greater than the diameter to that of the guide wire 7. Like the grooves 5 of the staple 1, the hole 9 in each tab 8 is sized to accomodate a guide wire 7, and is oriented directly above the groove 5 in the outer edge 6 of each of the staple's legs 3.

Alternatively, in embodiments not shown, the staple 1 can be formed without the tabs 8 or can be formed with the tabs 8 extending downward along the entire length of each staple leg 3. In the latter embodiment, each tab 8 essentially forms an outer edge 6 of each staple leg 3 so that a hole forms axially through the entire length of each staple leg 3. The resulting holes in the staple's legs 3 are capable of receiving guide wires 7 just as the recesses or grooves 5 of the staple 1 are.

Initially, a surgeon can insert guide wires 7 into bone, which remain in place while holes are drilled around the guide wires 7 using a specialized drill 10 that is capable of receiving the guide wires through its drill bit. The staple 1 is subsequently aligned with the guide wires 7 and inserted into the drilled holes.

The staple's holes 9 in its tabs 8 and grooves 5 along its legs 3 are sized to accommodate the passage of guide wires 7 while inserting the staple 1. The diameters of the holes 9, grooves 5, and guide wires 7 can vary depending on the surgical procedure but should be complimentary to each other. The staple 1 can be inserted over or along the guide wires 7 by placing the holes 9 in the tabs 8 over the wires 7, which automatically positions the grooves 5 along the legs 3 of the staple 1 to slide axially down the wires 7. Alternatively, for embodiments of the staple 1 which do not include tabs 8, the grooves 5 are aligned with the guide wires 7 and are sized to accommodate passage of the guide wires 7 for their insertion into the holes drilled around the guide wires 7. Similarly, for the embodiment of the staple 1 in which each tab 8 extends down the edge of each staple leg 3, thereby creating a hole along each staple leg 3, the hole 9 in each tab 8 is sized to receive a guide wire 7 therethrough. These methods prevent the loss of the pre-drilled holes in the bones prior to insertion of the staple 1, which could otherwise result from surrounding blood, debris, and soft tissue filling in the area.

The cannulated tabs 8 at the outer ends 4 of the bridge 2 of the staple 1 aid in the placement of the grooves 5 along the guide wires 7. For example, the proper positioning of the staple 1 can be verified using fluoroscopic images of the guide wires prior 7 to the drilling of holes or inserting the staple 1. The staples 1 can then be placed accurately and there is no need to re-drill the holes to properly insert the staple 1 and repair the bone. The procedure is greatly simplified and expedited, while the outcomes of the surgical procedures are improved as well.

Further, the bridge 2 of the staple 1 can be formed in a curved or slight "C" shape. As illustrated in FIGS. 1-5, the staple's bridge 2 is curved to the side so that its axis is substantially perpendicular to the staple's legs 3. In another embodiment, the staple's bridge 2 can be curved upward so that its axis is substantially parallel to the staple's legs 3. In yet another embodiment, the bridge 2 is formed in a substantially circular shape and is perpendicular to the staple's legs, as shown in FIGS. 7-9. In this embodiment, the bridge 2 is comprised of two "C" shaped extensions 21 that converge at the legs 3 of the staple 1.

The staple 1 can provide compression through a variety of means, including via manually compressible staples and staples made from memory metal. Besides aligning the staple 1 for proper placement to accept the guide wires 7, the tabs 8 and apertures 9 therethrough serve an additional helpful function for compression. In the case of manually compressible staples, a device for compressing the staple can be inserted into holes 9 in the tabs 8 and used to bring the legs 3 of the staple 1 together after the staple's insertion. Alternatively, in an embodiment in which the staple 1 is made from memory metal, the staple can be "memoried" in the compressed position with the legs 3 and ends of "C" shaped bridge 2 close together. In this case, the insertion tool can be used to separate the legs 3 from under the bridge 2 and along the grooves 5 located on the inner side of the legs 3, and push the legs 3 outward when activated. The staple 1 is inserted over the guide wires 7 before removing the insertion tool. Removal of the insertion tool will allow the staple 1 to return to its compressed position.

Also, staples made with shape memory alloys can have a memory transfer temperature that is close to body temperature. When the staple is attached with both ends of a broken bone the plate will contract from body heat or applied heat and retain its original shape, thereby exerting a compression force on the broken bone at the place of fracture.

The mechanism of compression can be greatly enhanced by forming the bridge 2 of the staple 1 in a slightly curved or slight "C" shape. For example, when the edges of the "C" are brought together, either by manual compression or the action of memory metal, the legs 3 of the staple 1 in their entirety move toward one another, thereby creating even compression.

With reference to FIG. 5, the staple 1 can include spikes, barbs, or other similar type of projections 11 along the legs 3 of the staple 1. The projections 11 can help stabilize the staple's placement in a bone.

FIGS. 6A-6I illustrate components of a surgical device system and a method for inserting the grooved and tabbed compression staple 1 according to the present invention. The surgical device system for repairing bone according to the present invention comprises grooved and tabbed staples 1 of varying widths and lengths that can be made of various materials; an adjustable width guide device 12; guide wires 7; drills 13 with drill bits of varying diameters; a depth gauge 14; an optional staple insertion/compression device; and an optional tamp or mallet.

Figure 6B:
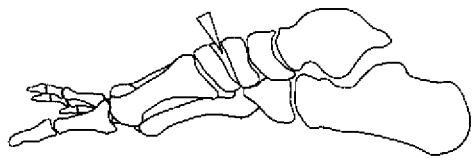
Figure 6C:
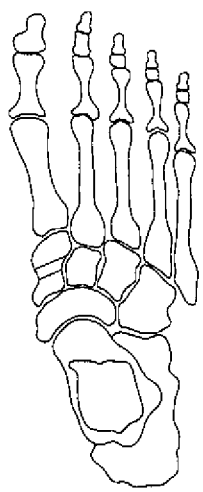
Figure 6D:
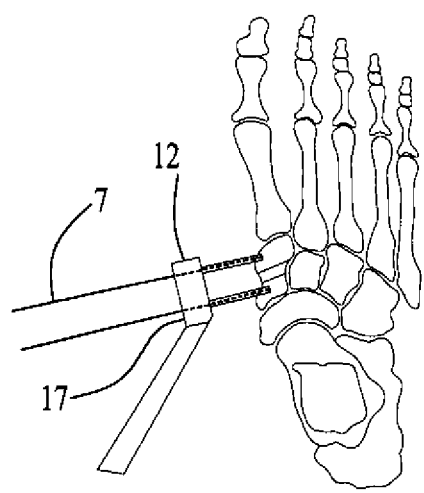

More specifically, as illustrated in FIG. 6D and in FIGS. 10-12, the guide device 12 includes two apertures 17 therethrough and is capable of accepting two guide wires 7 at a desired width across the bone fracture for their insertion. The width between the apertures 17 therethrough, which guides the two guide wires 7, is adjustable so that an appropriate bridge 2 width of the staple 1 can be selected depending on the needs during the surgery. For example, the width between the apertures 17 can be adjusted by slide-type or other mechanism in which the user can select the position, and lock into place, one or both of the apertures 17. As another example, a practitioner can select and lock the width of the guide device 12 itself using a slide-type or other mechanism, which in turn positions the width between the apertures 17.

Alternatively, the apertures 17 of the guide device 12 can be sized to accept and guide a drill 13. In this alternative embodiment, as shown in FIGS. 10-12, removable inserts 18 can be placed in the apertures 17 of the guide device 12. The removable inserts 18 are sized to accept the guide wires 7. The inserts 18 can subsequently be removed so that the guide device 12 can accept a drill 13 over the guide wires 7. Thus, the same guide device 12 can be used to both insert the guide wires 7 in a desired position and to guide a drill 13 with a drill bit that accepts the guide wires 7 to drill holes around the guide wires while the guide device 12 remains in the proper position. This embodiment is useful when it is necessary to use a device to guide the drill, in order to protect soft tissue while drilling.

As shown in FIG. 6F, a non-limiting embodiment of the depth gauge 14 can be placed over or along the side of a guide wire 7 of a known length and measure the depth of the wire's insertion at one end of the wire thereof. The difference in the position of the wire 7 in the depth gauge 14 before and after the wire's insertion indicates what length of the staple's legs 3 is appropriate to use. Thus, the depth gauge 14 simplifies measurement of the hole bored in the bone. The depth gauge 14 also determines whether the hole in the bone is at the desired depth. Alternatively, the guide wire 7 itself can have an indicator, such as a ruler-type indicator, that measures and displays the depth of its insertion and therefore determines the appropriate length of the fastener to use. The depth gauge 14 and guide wires 7 can use an electronic or manual means of displaying the depth measurement.

The drill 13 is shown in FIG. 6G, and includes a drill bit having an axially disposed aperture therethrough for accommodating the guide wire 7. Thus, the drill bit can be placed directly above the guide wire 7 and accepts the guide wire 7 through the axially disposed aperture of the drill bit. The drill is lowered toward the bone while surrounding the guide wire 7, and a hole can be drilled directly around the guide wire 7 in the desired area of the bone marked by the guide wire 7. The drill 13 allows for minimal incision conditions so that guide wires 7 stay in place during and after drilling the holes in the bone so that the staple may be inserted directly after the hole is made in the bone around the guide wire 7 without removal of the guide wire 7. As mentioned above, this prevents the problem of losing sight of the drilled holes due to their filling with debris. The drill 13 can use instrumentation that is power-driven or instrumentation that is manipulated manually by hand. The drill 13 can also be used with drill bits of varying diameters.

Figure 6E:
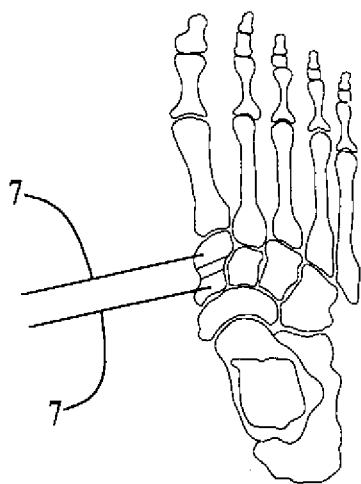

The following is a non-limiting description of a method of staple insertion. FIG. 6A shows the fractured bone. The fracture, osteotomy or fusion site is exposed, prepared and reduced using standard surgical dissection and reduction techniques as illustrated in FIGS. 6A to 6C. As shown in FIG. 6D, the adjustable guide device 12 is then set at the desired width, which is determined by positioning the guide 12 over the appropriate site. Guide wires 7 are then inserted through the guide device 12 while maintaining the guide in proper position. The guide wires 7 are adapted so that they can be inserted into the bone without requiring a pre-drilled hole prior to their insertion and lodging in the bone. As shown in FIG. 6E, the guide device 12 is removed and the position of the guide wires 7 can be confirmed clinically and fluoroscopically. As shown in FIG. 6F, a depth gauge 14 is used to assess the appropriate length of the staple's legs 3 by measuring the exposed length of the wire 7.

To seat the staple 1, holes will then be drilled around the guide wires 7 and into the bone using the drill 13 as described above, and as shown in FIG. 6G. As shown in FIGS. 6H and 6I, the appropriate sized tabbed and grooved staple 1 is aligned with the guide wires 7 and inserted into the bone. The guide wires 7 are subsequently removed. The compressing feature of the staple 1 can be activated automatically, manually or by the use of heat as needed, as described above. A tamp or mallet can be used as needed to further seat the staple. Final fluoroscopic images can be obtained to confirm placement and reduction before flushing and closing in the typical manner known in the art.

An alternative method for using a system in which the guide device 12 includes removable inserts 18 within the apertures 17 of the guide device 12 is also disclosed. According to a method using this guide device 12, both the guide wires 7 and the drill 13 can be guided into the bone using the guide device 12. A user can place the guide device 12 in a desired position over a bone fracture and then select the desired position or width between the apertures 17. Guide wires 7 can be inserted through the inserts 18 of the apertures 17 and into bone fragments. Once the guide wires 7 are in place, the inserts 18 can be removed. The user can then drill around the guide wires 7 and through the apertures 17 of the guide device 12 with a drill 13 as described above. After drilling, the guide device 12 is removed and a surgical staple 1 can be aligned with and guided by the guide wires 7 and inserted into the drilled holes in the bone. The guide wires 7 can be removed, and the staple 1 can be compressed and seated. As with the previous method, the positions of the guide wires 7 and the staple 1 can be confirmed fluoroscopically.

While the foregoing describes the present invention in relation to illustrations and examples, it is understood that it is not intended to limit the scope of the invention to the illustrations and examples described herein. On the contrary, it is intended to cover all alternative modifications and equivalents that may be included in the spirit and the scope of the invention as defined by the appended claims.

What is claimed is:

1. A surgical device system used for drilling at least two holes and inserting a first and second guidewire into bone, the improvement comprising:
   a surgical staple having a bridge connecting a first leg and a second leg;
   a first groove formed along the length of said first leg and open along said first leg, and a second groove formed along the length of said second leg and open along said second leg;
   a tab projecting from each of said legs, said tabs having apertures formed therein, each said tab positioned to align said aperture with said groove of the leg from which the tab is projecting;
   said apertures and said grooves sized and configured to receive and align a guide wire to direct said staple into bone;
   a first guide wire capable of insertion into the bone and capable of placement in said first groove and threaded through said corresponding aperture, and a second guide wire capable of insertion into the bone and capable of placement in said second groove and threaded through said corresponding aperture so that said staple can be guided into proper position; and
   a guide device having a first guide device aperture and a second guide device aperture, each of said guide device apertures capable of receiving a guide wire, and a sliding mechanism defined between said first and second guide device apertures, wherein said mechanism is adjustable such that a user can select a desired width to guide insertion of said guide wires into bone.

2. The surgical device system of claim 1, wherein each of said first and second guide device apertures of said guide device further comprise a detachably attachable insert, each of said inserts is capable of accepting guide wire.

3. The surgical device system of claim 1, further comprising a depth gauge, whereby a user can measure a length of insertion of the first and/or second guide wire and thereby select a desired length of said legs of said surgical staple for insertion into bone.

4. The surgical device system of claim 1, further comprising a drill, wherein at least a portion of said drill is capable of receiving a guide wire therethrough.

5. The surgical staple of claim 1, wherein the first groove and the second groove are U-shaped.

6. The surgical staple of claim 1, wherein the first groove and the second groove are L-shaped.

7. A surgical staple for holding bones together in which at least two holes have been drilled and a first and second guide wire have been inserted into the bone, the improvement comprising:
   a surgical staple having a bridge connecting a first and a second leg;
   a first groove formed along the length of said first leg and open along said first leg, and a second groove formed along the length of said second leg and open along said second leg;
   a tab projecting from each of said legs, said tabs having apertures formed therein, each tab positioned to align said aperture with said groove of the leg from which the tab is projecting;
   said apertures and said grooves sized and configured to receive and align a guide wire to direct said staple into bone; and,
   whereby said first guide wire inserted into the bone can be placed in said first groove and threaded through said corresponding aperture and the second guide wire inserted into the bone can be placed in said corresponding aperture so that said staple can be guided into proper position.

8. The surgical staple of claim 7, wherein said bridge is curved.

9. The surgical staple of claim 7, wherein said curved bridge forms a substantially circular shape so that the axis of said curved bridge is substantially perpendicular to said legs of said surgical staple.

10. The surgical staple of claim 7, wherein said legs have a plurality of projections protruding therefrom.

11. The surgical staple of claim 7, wherein said legs have at least an inner elevation and an outer elevation forming a groove along the length of each said leg for receiving and aligning a guide wire between each said inner and said outer elevations.

* * * * *